Figure 1:
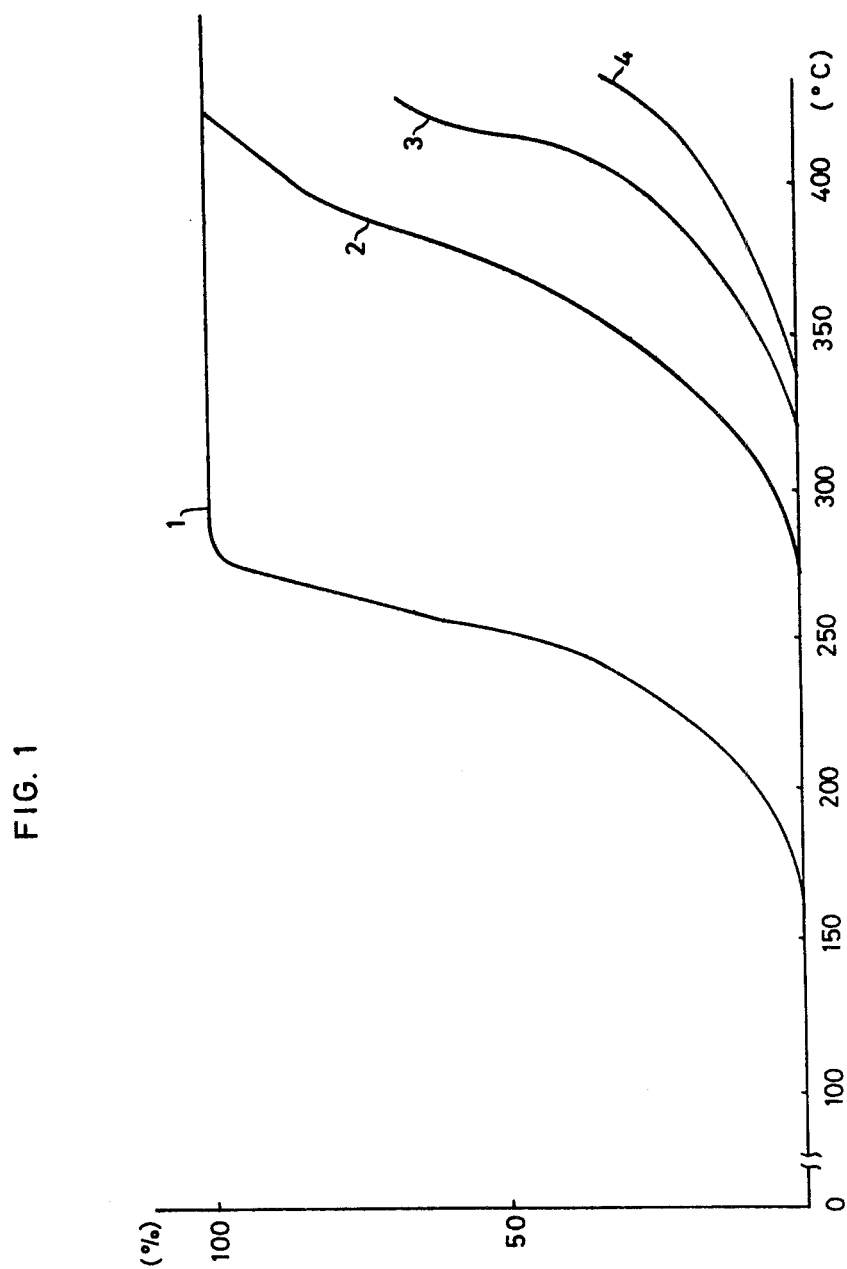

United States Patent [19]

Fujita et al.

[11] 4,077,971
[45] Mar. 7, 1978

[54] TETRAHYDROPHTHALIMIDE METHYL-2-PHENYLBENZATRIAZOLES

[75] Inventors: Taira Fujita, Nishinomiya; Kondo Yutaka, Tokyo; Nozomi Abe, Osaka; Takashi Akamatsu, Ashiya, all of Japan

[73] Assignees: Sumitomo Chemical Company, Limited, Osaka; Kyodo Chemical Company, Ltd., Tokyo, both of Japan

[21] Appl. No.: 604,992

[22] Filed: Aug. 15, 1975

[30] Foreign Application Priority Data

Aug. 15, 1974 Japan ................................ 49-93880

[51] Int. Cl.² .................. C07D 403/10; C07D 403/14; C08K 5/34
[52] U.S. Cl. ............................... 260/308 B; 252/300; 252/403; 106/176; 260/45.8 R; 536/76; 536/85; 536/58; 536/82; 536/56; 260/398.5
[58] Field of Search ..................... 260/308 B

[56] References Cited

FOREIGN PATENT DOCUMENTS 1,324,899  3/1963  France ............................. 260/308 B
1,169,859  11/1969  United Kingdom ............. 260/308 B

*Primary Examiner*—Alton D. Rollins
*Attorney, Agent, or Firm*—Wenderoth, Lind & Ponack

[57] ABSTRACT

A compound of the formula,

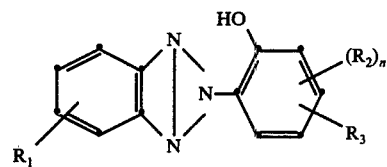

wherein $R_1$ is hydrogen or a halogen atom, $R_2$ is

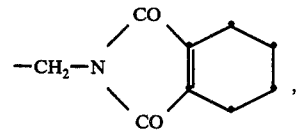

$R_3$ is hydrogen, an alkyl group, a cycloalkyl group or an aralkyl group, and n is an integer of 1 or 2, which is useful as ultraviolet absorber.

10 Claims, 9 Drawing Figures

TETRAHYDROPHTHALIMIDE METHYL-2-PHENYLBENZATRIAZOLES

The present invention relates to a novel ultraviolet absorber. More particularly, it relates to a novel v.-triazole compound (1,2,3-triazole compound) which is an effective component of the ultraviolet absorbers used for protecting light-sensitive organic substance from a harmful action of ultraviolet rays.

Many condensed v.-triazole compounds, particularly benzotriazole compounds, have already been well known as a ultraviolet absorber (for example, described in British Pat. No. 1,169,859), and some of them are commercially available. But, the ultraviolet absorbers of benzotriazole compounds are not always satisfactory because they are poor in ultraviolet ray-absorbing power or in light-fastness, or because they have a color to stain materials to be protected, or further because they are poor in thermal stability, resistance to sublimation, compatibility with or affinity to organic substances.

An object of the present invention is to provide novel ultraviolet absorbers which are superior in various properties usually required for ultraviolet absorbers, for example a ultraviolet ray-absorbing power, thermal stability and resistance to sublimation, and do not stain organic substances to be protected, and at the same time which are superior in compatibility with an affinity to said organic substances.

Another object of the present invention is to provide organic materials which are stable to ultraviolet rays.

Further object of the present invention will be apparent from the following description.

These objects can be achieved by (1) providing a novel 2-(2'-hydroxyphenyl)-benzotriazole of the formula (I),

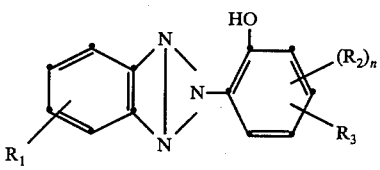

wherein $R_1$ is a hydrogen or halogen atom, $R_2$ is

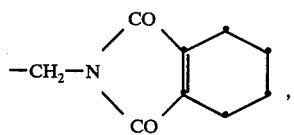

$R_3$ is a hydrogen atom, a lower alkyl, cycloalkyl or aralkyl group, and $n$ is an integer of 1 or 2, and (2) providing a method for preparing stable organic materials against ultraviolet rays, characterized by adding 2-(2'-hydroxyphenyl)-benzotriazole of the formula (I) to organic substances to be protected.

Figure 4:
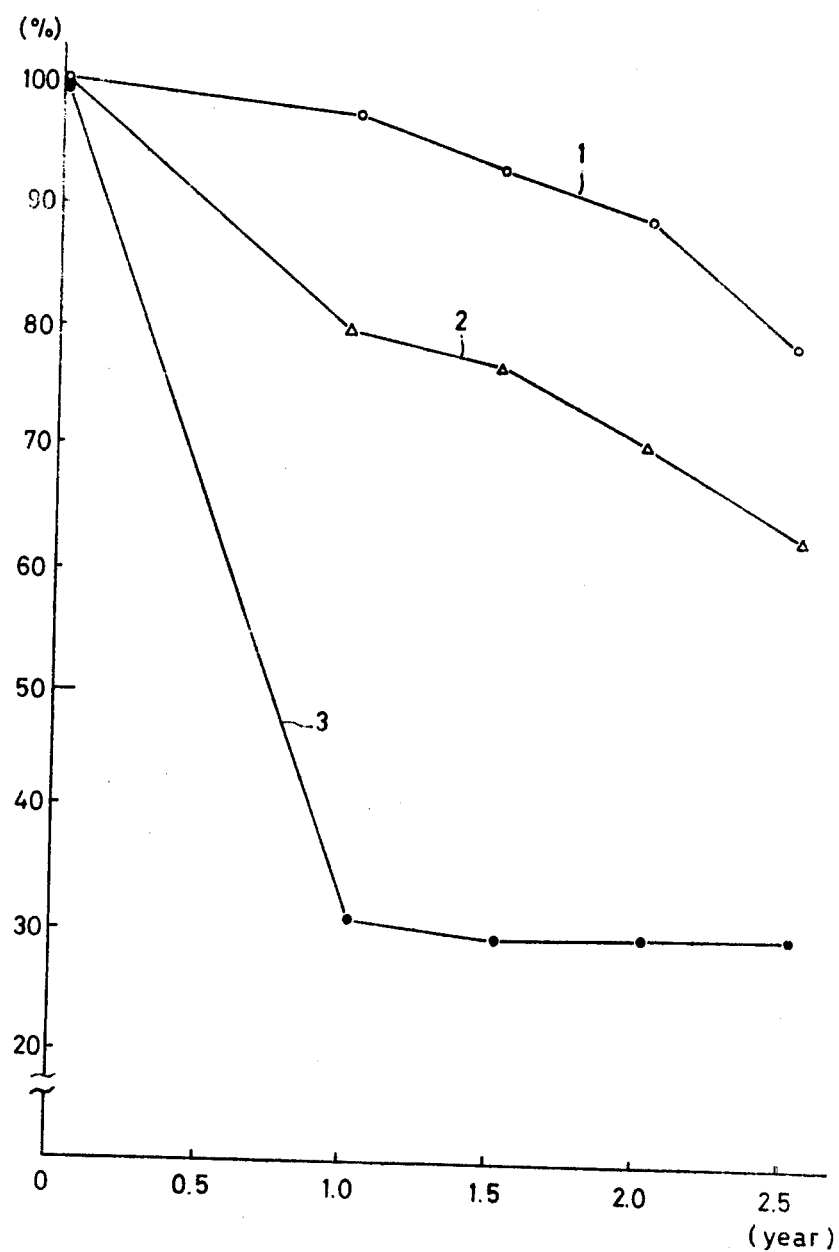
Figure 5:
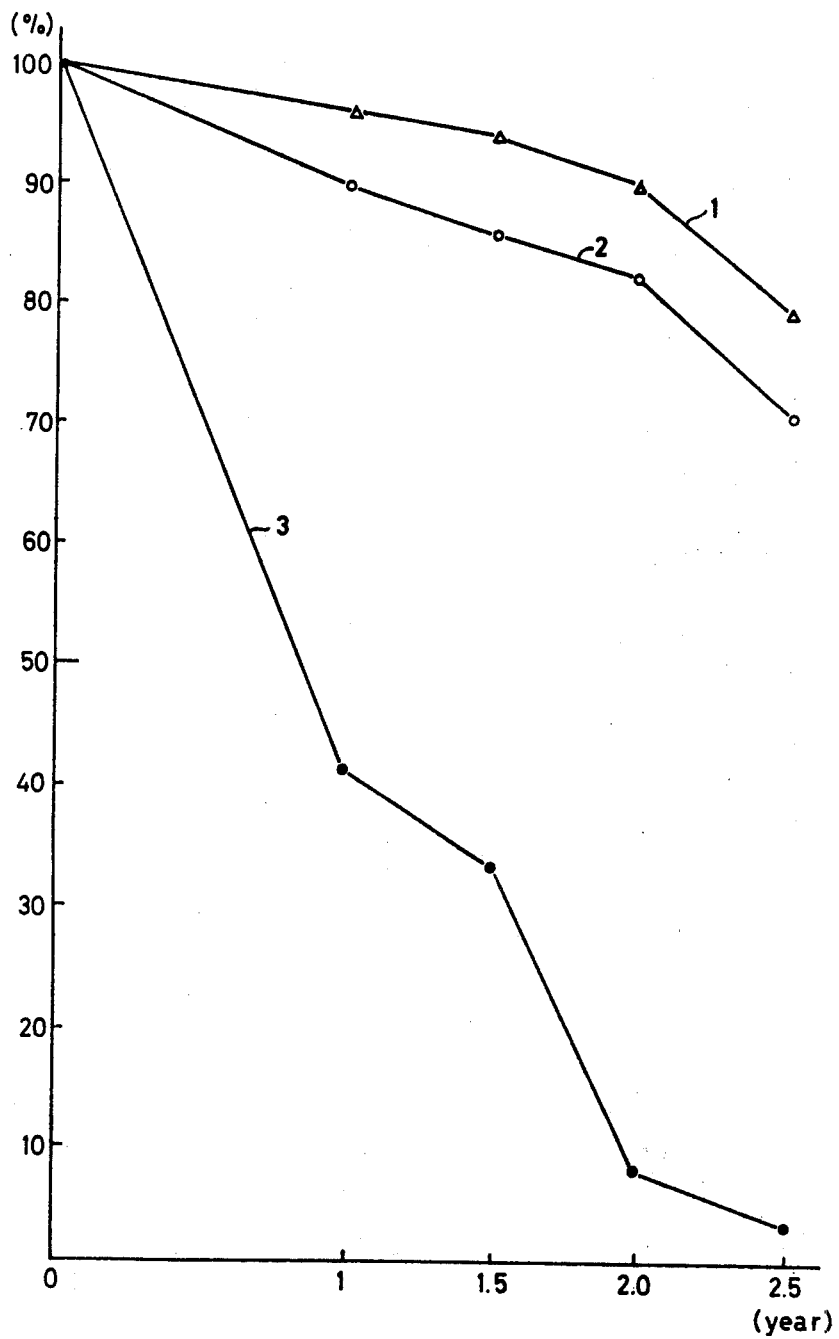
Figure 6:
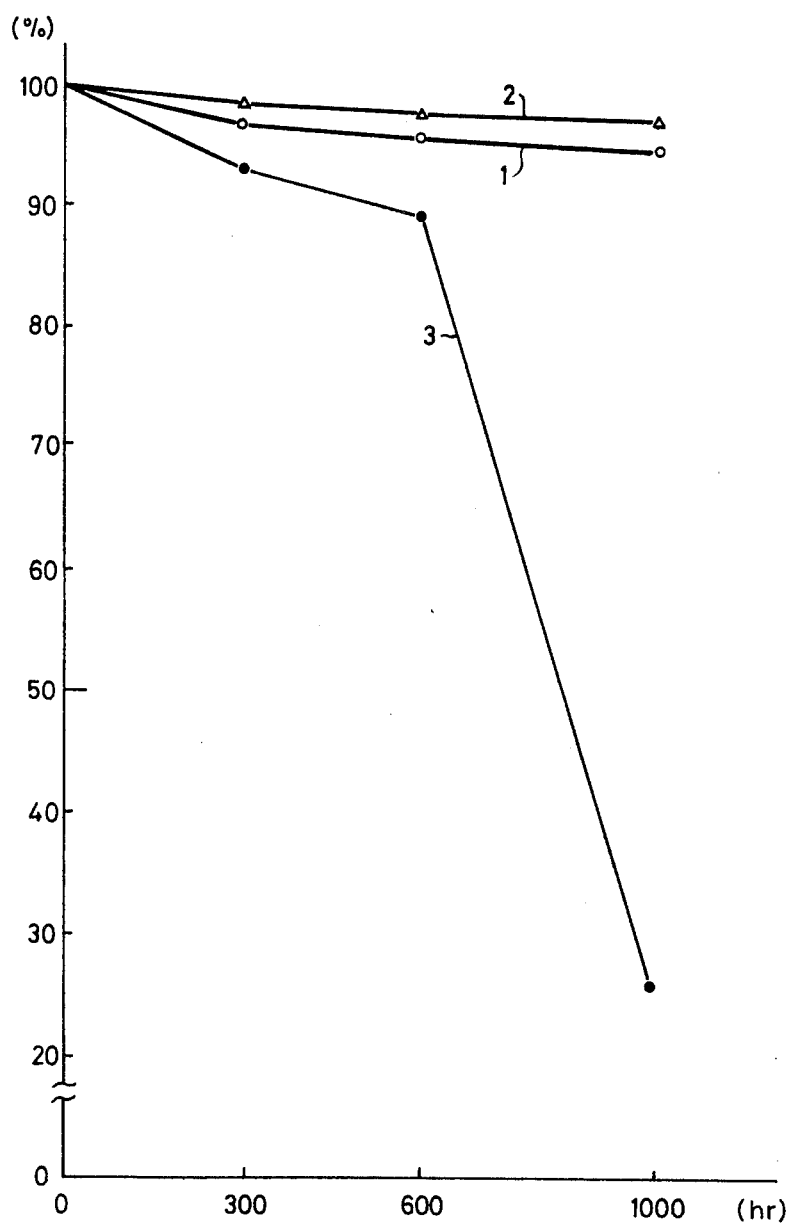
Figure 7:
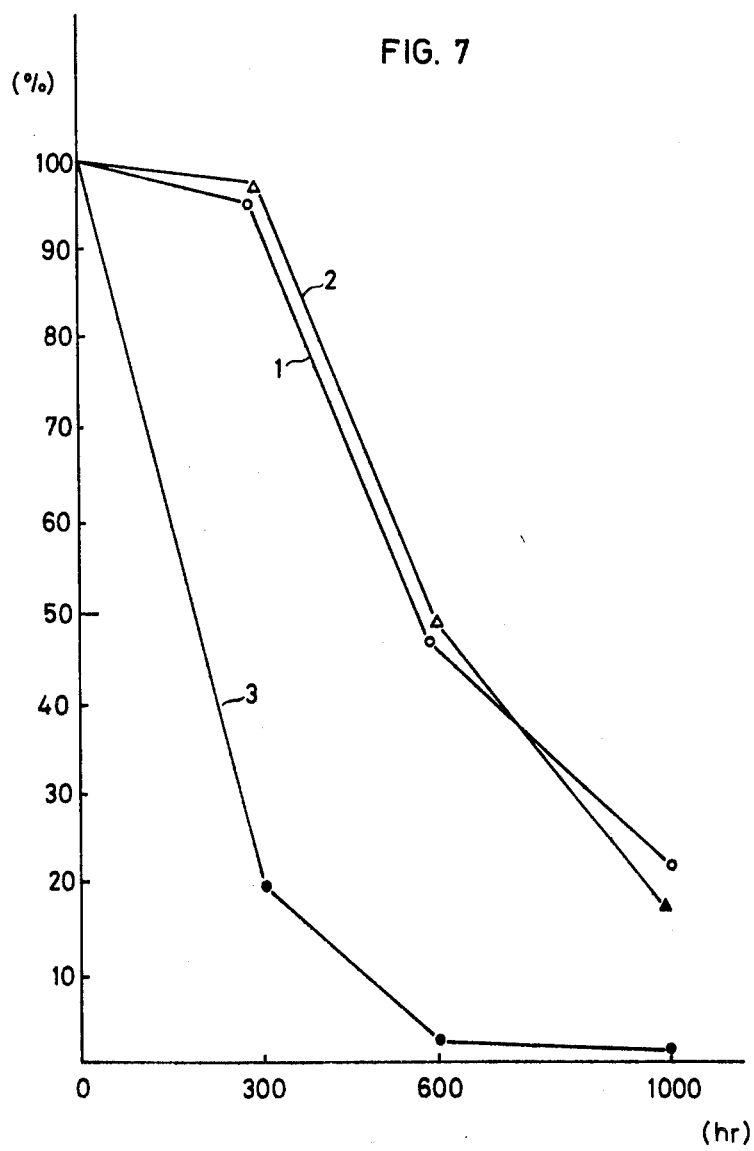
Figure 8:
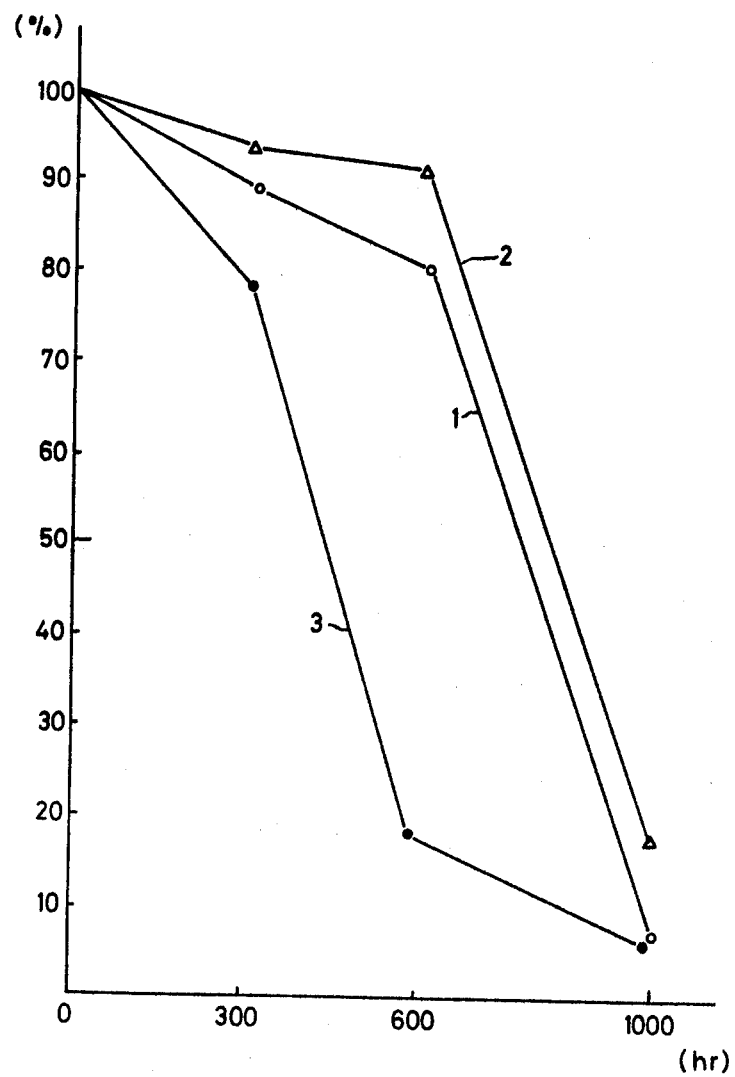

The present invention will be explained in more details as follows by referring partly to the accompanying drawings wherein FIG. 1 represents a non-volatility test result in Reference Example 2, FIG. 2 a change in elongation percentage in Example 9, FIG. 3 a change in breaking strength in Example 9, FIG. 4 a tensile strength retention in Example 13, FIG. 5 an elongation retention in Example 13, FIGS. 6 and 7 a tensile strength retention and elongation retention, respectively, in Example 14, FIG. 8 an elongation retention in Example 15, and FIG. 9 a yellowing index curve in Example 17.

The halogen atom referred to herein means a chlorine, bromine and iodine atom; the alkyl group means a $C_1$-$C_{18}$ alkyl group; the cycloalkyl group means a $C_5$-$C_7$ cycloalkyl group; and the aralkyl group means a $C_7$-$C_{12}$ aralkyl group.

The novel compound, 2-(2'-hydroxyphenyl)-benzotriazole, of the formula (I) can easily be obtained, (1) by reacting benzotriazole of the formula (II),

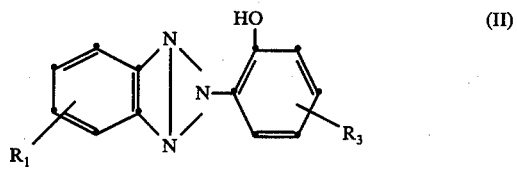

wherein $R_1$ and $R_3$ are as defined above, with tetrahydrophthalimide of the formula (III),

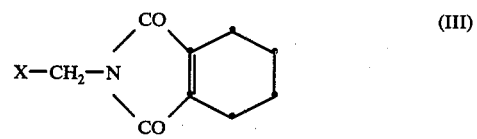

wherein X is a halogen atom or hydroxy group, at a temperature of $-10°$ C to 150° C in a suitable reaction medium (e.g. an acid or organic solvent) in the presence of a suitable additive (e.g. an acid, alkali, dehydrating agent), or (2) reacting benzotriazole of the formula (II) with tetrahydrophthalimide of the formula (IV),

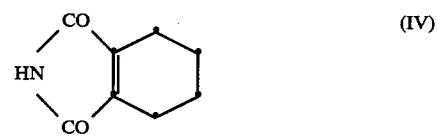

at 0° to 50° C in sulfuric acid in the presence of formaldehyde or dichloromethyl ether, or (3) by reacting o-substituted azo compounds of the formula (V),

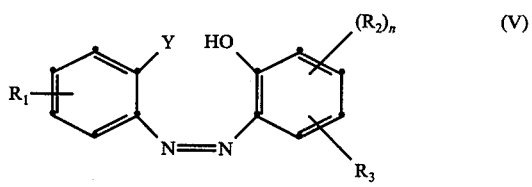

wherein $R_1$, $R_2$, $R_3$ and $n$ are as defined above, and Y is a $-NH_2$ or $-NO_2$ group, with an oxidizing or reducing agent.

The method will be described in more details as follows.

PREPARATION 1

The present compound (I) can be obtained by subjecting benzotriazole compound (II) and N-methylol tetrahydrophthalimide (X is a hydroxy group in the formula (III)) to a dehydration-condensation reaction at about $-10°$ C to 150° C for about 1 to 10 hours in sulfuric acid (80 - 100%), acetic anhydride-glacial acetic acid mixture or polyphosphoric acid (100 - 130%), a more preferred reaction temperature being about 0° C to 30° C for the sulfuric acid, about 90° C to 110° C for the acetic acid series solvent and about 60° C to 150° C for the polyphosphoric acid. The sulfuric acid may be replaced by a suitable inert solvent (for example, nitrobenzene, toluene, monochlorobenzene, o-dichlorobenzene and the like) to which p-toluenesulfonic acid or anhydrous aluminum chloride has been added. In this case, the reaction is carried out at elevated temperatures, preferably 30° C to 150° C.

Further, the compound (I) can be obtained by subjecting the compound (II), tetrahydrophthalimide (IV) and para-formaldehyde or formaline solution to the dehydration-condensation reaction at about −10° C to 50° C, preferably at about 0° C to 30° C in sulfuric acid. Still further, the compound (I) can be obtained by carrying out the reaction at about 80° C to 130° C using a reaction medium such as water or polar solvent in place of the sulfuric acid.

PREPARATION 2

The present compound (I) can be obtained by subjecting the compound (II) and N-halogenated methyltetrahydrophthalimide (corresponding to the compound of the formula (III) wherein X is a halogen atom) to the Friedel-Crafts type reaction at, usually, elevated temperatures, preferably about 50° C to 150° C for about 2 to 15 hours in an inert solvent (for example nitrobenzene, monochlorobenzene and the like) to which a catalyst (for example anhydrous aluminum chloride, anhydrous zinc chloride, boron fluoride, hydrogen fluoride, polyphosphoric acid and the like) has been added. Further, the compound (I) can be obtained by subjecting the compound (II), tetrahydrophthalimide (IV) and dichloromethyl ether to the condensation reaction at about 0° C to 50° C in sulfuric acid.

PREPARATION 3

The compound (I) can be obtained by reacting o-nitroazo compounds of the formula (V-a),

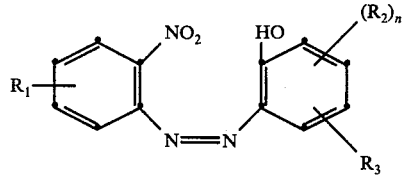

wherein $R_1$, $R_2$, $R_3$ and $n$ are as defined above, with a reducing agent such as zinc, aluminum, glucose or the like at 0° C to 100° C in a suitable reaction medium such as water or a polar solvent. The compound of the formula (V-a) is obtained by subjecting said phenols and o-nitroanilines to the conventional diazotization and coupling reactions. Further, the compound (I) can be obtained by oxidizing o-aminoazo compounds of the formula (V-b),

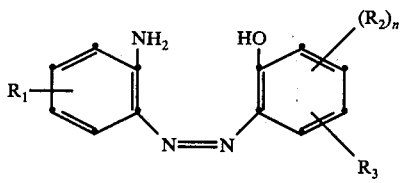

wherein $R_1$, $R_2$, $R_3$ and $n$ are as defined above, with an oxidizing agent such as ammoniac copper sulfate, hydrogen peroxide or the like at 10° C to 100° C in water or polar solvent.

The compound (V-b) is obtained by reducing the compound (V-a) with ammonium sulfide or the like. Said phenols are easily obtained by reacting a phenol derivative of the formula,

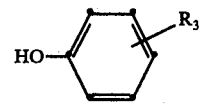

wherein $R_3$ is as defined above, with tetrahydrophthalimide of the formula (IV) in the presence of formaldehyde such as paraformaldehyde or by reacting the phenol derivative with tetrahydrophthalimide of the formula (III).

Examples of the present compounds obtained according to the above-mentioned process are summarized in Table 1. In the Table, the symbols, $R_1$, $R_2$, $R_3$ and $n$ are tabulated, and $R_2$ represents a position alone at which the group,

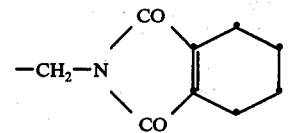

is attached to the benzene ring.

Table 1

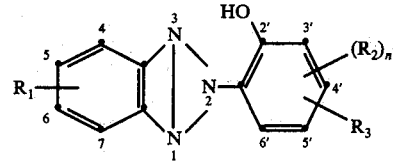

| UVA No. | $R_1$ | $R_2$ | $R_3$ | $n$ | $\lambda_{max}$ (m$\mu$) | m.p. (° C) |
|---|---|---|---|---|---|---|
| 1 | H | 3' | 5'-CH$_3$ | 1 | 341 | 170.2 |
| 2 | 5-Cl | " | " | " | 342 | 179 |
| 3 | H | " | 5'-t-C$_4$H$_9$ | " | 343 | 172 |
| 4 | 5-Cl | " | " | " | 345 | 181 |
| 5 | H | " | 5'-n-C$_8$H$_{17}$ | " | 343 | 178 |
| 6 | 5-Cl | " | " | " | 345 | 183 |
| 7 | H | " | 5'-n-C$_9$H$_{19}$ | " | 343 | 180 |
| 8 | 5-Cl | " | " | " | 346 | 184 |
| 9 | " | 5' | 3'-CH$_3$ | " | 342 | 195 |
| 10 | H | 3' | 5'-CH$_2$C$_6$H$_5$ | " | 339 | 110 |
| 11 | " | " | 5'-C(CH$_3$)$_2$—C$_6$H$_5$ | " | 340 | 186 |
| 12 | " | " | 5'-CH(CH$_3$)—C$_6$H$_5$ | " | 340 | 148 |
| 13 | 5-Cl | " | 5'-CH$_2$C$_6$H$_5$ | " | 345 | 141 |
| 14 | " | 3'5'-bis | H | 2 | 347 | 185 |
| 15 | H | " | " | " | 340 | 175 |
| 16 | 5-Cl | " | 4'-CH$_3$ | " | 350 | 178 |
| 17 | H | 5' | H | 1 | 338 | 123 |
| 18 | 5-Cl | " | 3'-i-C$_3$H$_7$ | " | 342 | 190 |
| 19 | " | " | 4'-CH$_3$ | " | 347 | 130 |

Of these compounds shown in Table 1, preferred compounds are 2-(2'-hydroxyphenyl)-benzotriazoles of the formula (I) wherein $R_1$ is a hydrogen or chlorine atom, the position of $R_2$ is 3' and/or 5' and $R_3$ is a $C_1$-$C_9$ alkyl, phenyl $C_1$-$C_3$ alkyl or, when $R_2$ is attached to both 3'- and 5'-positions, a hydrogen atom. Among those preferred compounds, the most preferred is a compound of the formula (I) wherein $R_3$ is a $C_1-C_4$ alkyl group.

The compounds of the formula (I) thus obtained have the excellent property that they absorb efficiently ultraviolet rays having a wave-length of 310 to 380 mμ in the ultraviolet region (300 to 400 mμ) which deteriorates or destroys organic substances particularly, but they never absorb any ray having wavelengths longer than 400 mμ. Therefore, they have a strong protective action against ultraviolet rays and give little or no coloration.

The ultraviolet absorbers of the present invention which contain as an effective component the compounds of the formula (I) can be applied according to a conventional method to any organic high polymer material, particularly, to all synthetic polymers, for example addition polymers, particularly polymers resulting from compounds having an ethylenic double bond such as polyvinylchloride, polyvinylidene chloride, styrol polymers, diene polymers, copolymers thereof, polyethylene, polypropylene, polyacrylonitrile compounds particularly polymethylmethacrylate or polyacrylonitrile; condensation polymers for example polyesters such as polyethylene glycol terephthalate, polyamides such as polycaprolactam, and mixed polymers for example polyester resins such as addition polymers between unsaturated polyesters and oleffins such as styrol or methylmethacrylate; and natural polymers or their modified products such as cellulose, cellulose esters and cellulose ethers. There are exemplified natural products such as oil and fat, wax, resin, cellulose, wool, silk, flax and the like; semiartificial products such as cellulose acetates, celluloid, lacquor and the like. The molecular weight of these polymers may be between 1,000 and several millions.

The v.-triazole compounds of the invention may be applied to those polymers in various ways according to the kind of the polymers. For example, at least one of said compounds and, in some cases, additives such as a softening agent, antioxidant, thermal stabilizer, and pigment are added together to molten polymers prior to or during molding according to the conventional procedures; or said compound is dissolved in the corresponding monomer before the polymerization reaction (in this case, said compound and the monomer must not react with each other); said compounds, the additives and the polymers are dissolved in a solvent and then the solvent is evaporated; said compounds are applied to film or line in the form of aqueous dispersion; or a neutral solution of the compounds is mixed directly with liquid substrates to be protected.

As mentioned above, the present compounds are superior to other common ultraviolet absorbers in the thermal stability (resistance to decomposition and sublimation), compatibility and affinity and can be used without problem at temperatures as high as more than 350° C. Therefore, they are a protective agent which is most suitable for fabricating or molding said synthetic polymers at high temperatures. For example, the present compounds can be satisfactorily used without any danger of decomposition and sublimation even when added to molten polymers of high temperature. The compounds have also another characteristic that they show little or no blooming and bleeding even when added in an increased amount. Therefore, the compounds can also be used very advantageously for spinning. The present compounds of the above-mentioned formula can be used very effectively even in an extremely small amount, for example 0.001 to 0.1% by weight based on the organic substances to be protected from ultraviolet rays.

The present invention will be illustrated in more details with reference to the following examples and reference examples, which are not however to be interpreted as limiting the present invention thereto.

EXAMPLE 1

Preparation of UVA No. 1: 2-[2'-hydroxy-5'-methyl-3'-(3", 4", 5",6"-tetrahydrophthalimide methyl)-phenyl]benzotriazole 27.6 g of o-nitroaniline were heated in a mixture of 46.8 g of water and 62.5 g of a 35% hydrochloric acid at about 80° C. The resulting hot solution was poured into 250 g of ice under vigorous stirring to deposite o-nitroaniline hydrochloride as fine crystals. Then 76.0 g of a 20% aqueous sodium nitrite solution was added thereto at 0° C to 5° C and the mixture was stirred for 3 hours. After an excess of sodium nitrite was removed with sulfamic acid, the solution was filtered through celite and the filtrate was taken as a diazo liquor.

Separately from this, 21.6 g of p-cresol were suspended in 1,000 g of water containing 48 g of sodium acetate and 10 g of caustic soda and then 100 g of benzene were added thereto. Coupling reaction was then carried out by adding dropwise the diazo liquor to the suspension during which the suspension was kept at 0° C to 5° C with an addition of ice. To the resulting reddish brown crystals were added 250 g of methanol and then 120 g of a 30% aqueous caustic soda at room temperature.

Further, 55 g of zinc powder were added thereto gradually, and the resulting mixture was refluxed under heating for 2.5 hours. The reaction solution was filtered hot to remove the unreacted zinc powder, and the filtrate was poured into a dilute aqueous hydrochloric acid at less than 20° C and then adjusted to pH 1. The resulting crude cake was extracted with toluene, and the toluene extract was dehydrated and concentrated until crystals deposited. The resulting crystals were recrystallized from a benzene-methanol mixed solvent to obtain 35.0 g of white crystals (yield 78.0%).

22.5 g of 2-(2'-hydroxy-5'-methylphenyl)-benzotriazole thus obtained were dissolved in 300 c.c. of a conc. sulfuric acid, and 18 g of N-methylol tetrahydrophthalimide were added thereto in small portions at 0° C to 10° C. The mixture was reacted at the same temperature for 3 to 4 hours. Then the reaction solution was discharged into 1 liter of ice water, filtered, washed with water, dried and recrystallized from ethyl acetate to obtain 36 g of white crystals (yield 90%).

m.p. 170.2° C $\lambda_{max}$: 341 mμ ($\epsilon_{max}$ 1.6 × 10$^4$) (in dioxane)

Elementary Analysis:

Calculated (%) as $C_{22}H_{20}N_4O_3$; C; 68.04, H; 5.15, H; 14.43; Found (%) C; 67.92, H; 5.29, N; 14.40.

EXAMPLE 2

Preparation of UVA No. 2

2-(2'-Hydroxy-5'-methylphenyl)-5-chloro-benzotriazole was prepared in the manner similar to that described in Example 1 using 1-nitro-5-chloroaniline in place of o-nitroaniline. Then 26 g of the compound, 13.3 g of anhydrous aluminum chloride were dissolved in 100 ml of nitrobenzene, and 18 g of N-methylol tetrahydrophthalimide were added thereto in small portions at 30° to 40° C. The mixture was heated at the same temperature for 10 to 12 hours to complete the reaction.

Water was added thereto and the mixture was subjected to steam distillation to distill off the nitrobenzene. The residue was filtered to obtain a cake, which was washed with water, dried and recrystallized from ethyl acetate to give 31.6 g of white crystals (yield 75%).

m.p. 179.2° C $\lambda_{max}$: 342 m$\mu$ ($\epsilon_{max}$ 1.6 × 10$^4$) (in dioxane)

Elementary analysis:
Calculated (%) as $C_{22}H_{19}N_4O_3Cl$;
C; 62.49, H; 4.50, N; 13.25, Cl; 8.40;
Found (%) C; 62.35, H; 4.49, N; 13.08, Cl; 8.35.

EXAMPLE 3

Preparation of UVA No. 3

2-(2'-Hydroxy-5'-t-butylphenyl)-benzotriazole was prepared in the manner similar to that described in Example 1 using p-t-butylphenol in place of p-cresol. Then, 26.7 g of the compounds, 18.1 g of N-methylol tetrahydrophthalimide were added to 300 ml of monochlorobenzene, and further 2.0 g of p-toluenesulfonic acid were added thereto. The mixture was refluxed for 5 to 8 hours, and thus the dehydration reaction was completed.

The reaction solution was steam-distilled to remove the monochlorobenzene, filtered, washed with water, dried and recrystallized from methyl isobutyl ketone to obtain 30 g of white crystals (yield 70%).

m.p. 172.0° C $\lambda_{max}$: 343 m$\mu$ ($\epsilon_{max}$ 1.6 × 10$^4$) (in dioxane)

Elementary analysis:
Calculated (%) as $C_{25}H_{26}N_4O_3$;
C; 69.77, H; 6.05, N; 13.02;
Found (%) C; 69.81, H; 6.02, N; 13.10.

EXAMPLE 4

Preparation of UVA No. 1

22.5 g of 2-(2'-hydroxy-5'-methylphenyl)-benzotriazole and 15 g of tetrahydrophthalimide were dissolved in 300 ml of a concentrated sulfuric acid and 3.3 g of paraformaldehyde were added thereto in small portions at 0° C to 10° C. The mixture was reacted at the same temperature for 3 to 4 hours. The reaction solution was discharged into 1 liter of ice water, filtered, washed with water, dried and recrystallized from ethyl acetate to obtain 36 g of white crystals. The resulting compound agreed completely with that obtained in Example 1 in melting point and elementary analysis.

EXAMPLE 5

Preparation of UVA No. 10

30 g of 2-(2'-hydroxy-5'-benzylphenyl)-benzotriazole obtained in the manner similar to that described in Example 1 using p-benzylphenol in place of p-cresol were dissolved in 300 ml of a concentrated sulfuric acid and 18 g of N-methylol tetrahydrophthalimide were added thereto in small portions at 0° to 10° C. The mixture was reacted at the same temperature for 3 to 4 hours. Thereafter, the reaction solution was discharged into 1 liter of ice water, filtered, washed with water, dried and recrystallized from methanol to obtain 43 g of white crystals (yield 90%).

m.p. 110° C $\lambda_{max}$: 339 m$\mu$ (in dioxane)

Elementary analysis:
Calculated (%) as $C_{28}H_{24}N_4O_3$;
C; 72.4, H; 5.2, N; 12.1;
Found (%) C; 72.1, H; 5.0, N; 12.3.

EXAMPLE 6

The compound of the invention (UVA No. 1) was added to a 25% urethane dope (a mixture of 25 parts of polyurethane resin, 3.75 parts of dimethylformamide (DMF) and 71.25 parts of tetrahydrofuran (THF)), a proportion of the compound to the polyurethane resin being as described in Table 2. The urethane dope was then applied onto nylon film, and the coated film was dried at 45° C. for 1 hour in a dryer and then cut into sheet of 10 cm × 5 cm in size. The sheet thus obtained showed a very good fastness on the light fastness test using a Fade-O-Meter (made by Toyo Seiki Co., Ltd.). The anti-yellowing effects of the UVA No. 1 and other compounds on polyurethane resin are summarized in Table 2.

Table 2

| Ultraviolet absorbers UVA No. | % | Exposure time and staining degree | | | | Degree of blooming |
|---|---|---|---|---|---|---|
| | | O(min) | 15(min) | 30(min) | 45(min) | |
| No addition | 0 | 0 | 5 – 6 | 6 – 7 | 8 | |
| No. 1 | 1.0 | 0 | 2 – 3 | 3 | 4 | No blooming |
| | 2.0 | 0 | 1 | 2 – 3 | 3 | " |
| No. 2 | 1.0 | 0 | 2 | 2 | 3 | " |
| | 2.0 | 0 | 1 | 1 – 2 | 2 | " |
| No. 3 | 1.0 | 0 | 2 | 3 | 5 | " |
| | 2.0 | 0 | 1 | 1 – 2 | 3 – 4 | " |
| No. 4 | 1.0 | 0 | 1 | 3 | 4 | " |
| | 2.0 | 0 | 0 – 1 | 2 | 3 | " |
| No. 5 | 1.0 | 0 | 2 | 3 | 5 | " |
| | 2.0 | 0 | 1 | 2 | 3 | " |
| No. 14 | 1.0 | 0 | 1 | 2 – 3 | 3 – 4 | " |
| | 2.0 | 0 | 0 – 1 | 1 – 2 | 2 | " |
| No. 17 | 1.0 | 0 | 1 | 2 | 4 | " |
| | 2.0 | 0 | 1 | 1 – 2 | 2 | " |
| No. 18 | 1.0 | 0 | 2 | 4 | 5 | " |
| | 2.0 | 0 | 1 | 2 | 3 – 4 | " |
| No. 19 | 1.0 | 0 | 2 | 3 | 4 | " |
| | 2.0 | 0 | 2 | 2 | 3 | " |
| Well known compound 1 | 1.0 | 0 | 3 | 4 – 5 | 5 – 6 | High blooming |

Table 2-continued

| Ultraviolet absorbers UVA No. | % | Exposure time and staining degree 0(min) | 15(min) | 30(min) | 45(min) | Degree of blooming |
|---|---|---|---|---|---|---|
| | 2.0 | 0 | 2 | 4 | 5 | " |
| Well known | 1.0 | 0 | 3 | 5 | 7 | " |
| compound 2 | 2.0 | 0 | 2 | 5 | 6 | " |

Note:
The judgement was made visually, and larger numbers mean a larger degree of staining.

Well known compound 1

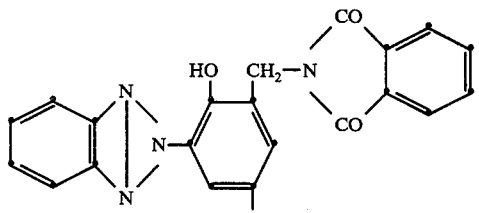

Well known compound 2

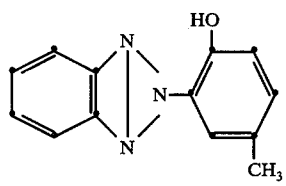

EXAMPLE 7

Polyethylene terephthalate resin was coated with ultraviolet absorbers by blending 100 parts of the resin and 2 parts of the absorbers in a mixer for domestic use. The blend thus obtained was formed into a relatively thick sheet by the conventional melt extrusion, orientated under heating by stretching four times in lengthwise and crosswise directions each, and then fixed at higher temperatures. Thus, polyester film of 0.1 mm in thickness was prepared. The film was exposed outdoors and then measured for the staining-inhibiting effect. The results obtained are shown in Table 3.

Table 3

| UVA | Exposure time (year) 1 | 2 | 3 |
|---|---|---|---|
| No addition | colorless | slight yellow | yellow |
| Well known compound 1 | " | colorless | slight yellow |
| No. 3 | " | " | extremely slight yellow |
| No. 4 | " | " | " |

EXAMPLE 8

The film prepared in Example 7 was hung in a room and tested for blooming. Blooming was observed after only seven days for the well known compound 1, but was not observed for the present compounds Nos. 3 and 4 even after six months. The results mean that the present compounds have an excellent compatibility with polyester resins.

EXAMPLE 9

| A mixture comprising, | | |
|---|---|---|
| polyvinyl chloride ($\bar{p}$ = 800) | 100 | parts |
| KV-33E (cadmium-barium liquid composite stabilizer produced by Kyodo Chemical Co.) | 1.3 | parts |
| cadmium stearate | 0.4 | part |
| barium stearate | 0.2 | part |
| epoxidized soybean oil | 1.0 | part |
| ultraviolet absorber | 0.1 | part | was kneaded at 150° C for 5 minutes on a 6-inch roller, and then formed into sheet of 0.5 mm in thickness. The sheet was cut into dumb-bell No. 1 test pieces. The test pieces showed a very good fastness on the outdoor exposure test. After the exposure, the test pieces were tested for the elongation retention and breaking strength retention by means of an extensometer.

Figure 2:
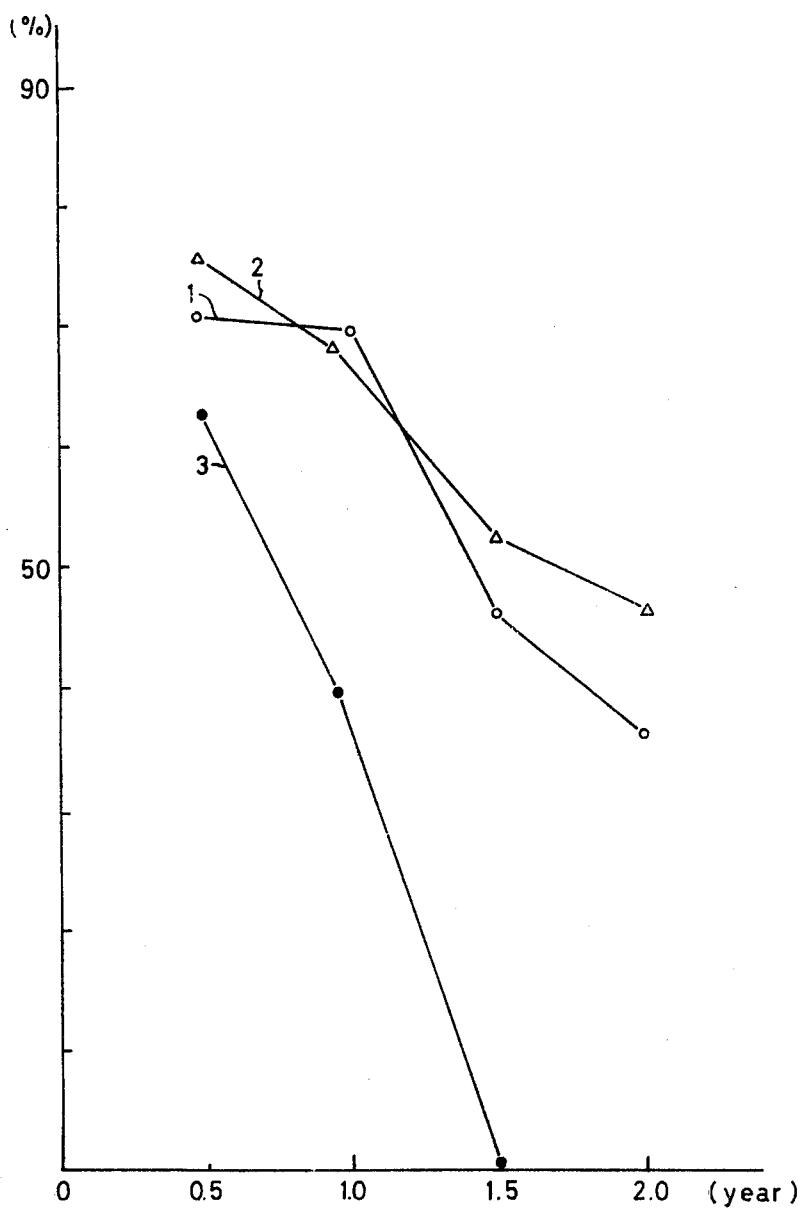
Figure 3:
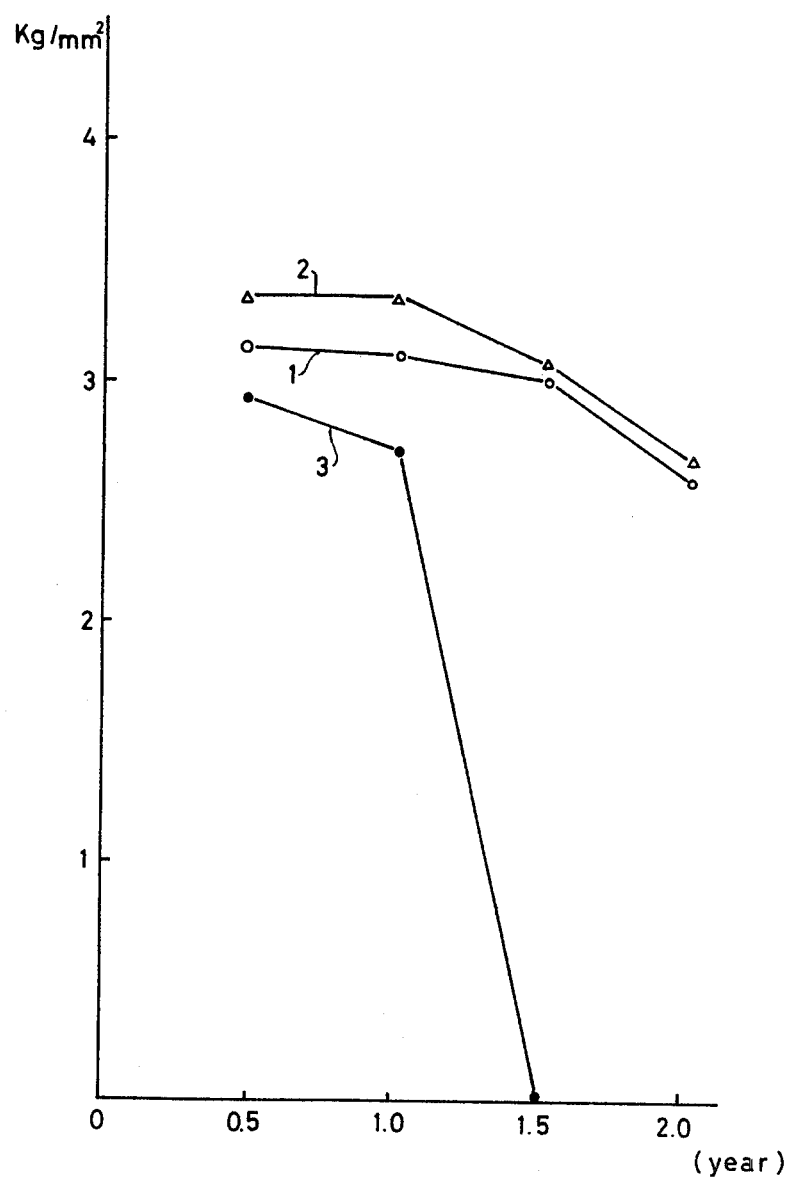

The results are shown in FIG. 2 (change in elongation retention) and in FIG. 3 (change in breaking strength retention). The result shows that the present compound (UVA No. 1) has a very superior effect. The tension test condition is as follows:

| extensometer | (made by Toyo Seiki Co., Ltd.) |
|---|---|
| Strography-C tension rate | .10 mm/min. |
| tension temp. | 20° C |

In the FIGS. (1), (2) and (3) are a curve obtained with the well known compound 1, the present compound UVA No. 1, and a blank test, respectively. The ordinates in FIGS. 2 and 3 represent the retension (%) and kg/cm², respectively and the abscissa in each figure represents the exposure time (years).

EXAMPLE 10

| A mixture comprising, | | |
|---|---|---|
| polyvinyl chloride ($\bar{p}$ = 1,100) | 100 | parts |
| DOP | 50 | parts |
| KV-33K (cadmium-barium type stabilizer for polyvinyl chloride for agricultural use, produced by Kyodo Chemical Co.) | 1.5 | parts |
| cadmium stearate | 0.6 | part |
| barium stearate | 0.2 | part |
| ultraviolet absorber | 0.1 | part | was kneaded on a 6-inch roller at 150° C for 5 minutes and then formed into sheet of 0.5 mm in thickness. The sheet was exposed outdoors and then tested for the staining-inhibiting effect. The results are shown in Table 4.

Table 4

| UVA | Exposure time (month) 6 | 12 | 18 | 24 | 30 | Remarks |
|---|---|---|---|---|---|---|
| No addition | a little yellow | brown spot | black brown | black brown | black | |

Table 4-continued

| UVA | Exposure time (month) | | | | | Remarks |
|---|---|---|---|---|---|---|
| | 6 | 12 | 18 | 24 | 30 | |
| Well known compound 1 | extremely slight yellow | same as left | slight yellow | same as left | a little yellow | blooming |
| Well known compound 2 | extremely slight yellow | same as left | slight yellow | same as left | a little yellow | |
| UVA No. 2 | extremely slight yellow | same as left | same as left | slight yellow | same as left | |
| UVA No. 5 | extremely slight yellow | same as left | slight yellow | same as left | same as left | |
| UVA No. 7 | extremely slight yellow | same as left | slight yellow | same as left | same as left | |

As can be seen from Table 4, the sheet with ultraviolet absorbers is much more stable and much less stained than that without the absorbers. In the kneading process above-mentioned, there may be added, if necessary, antioxidants, other common ultraviolet absorbers, pigments, coloring matters or fluorescent brightening agents.

EXAMPLE 11

| A mixture comprising, | | |
|---|---|---|
| polyvinyl chloride ($\bar{p}$ = 800) | 100 | parts |
| KS-6E (dibutyl tin maleate type stabilizer, produced by Kyodo Chemical Co.) | 3 | parts |
| LX-6 (lubricant, produced by Kyodo Chemical Co.) | 0.8 | part |
| ultraviolet absorber | 0.2 | part | was kneaded on a 6-inch roller at 160° C. for 5 minutes, and then formed into sheet of 0.5 mm in thickness. The sheet was exposed outdoors and then tested for the staining-inhibiting effect. The results are shown in Table 5.

Table 5

| UVA | Exposure time (month) | | | | |
|---|---|---|---|---|---|
| | 6 | 12 | 18 | 24 | 30 |
| No addition | slight yellow | same as left | a little black yellow | a little black brown | black brown |
| Well known compound 1 | colorless | same as left | same as left | a little yellow | same as left |
| UVA No. 2 | colorless | same as left | same as left | same as left | same as left |
| UVA No. 5 | colorless | same as left | same as left | same as left | slight yellow |
| UVA No. 7 | colorless | same as left | same as left | same as left | slight yellow |
| UVA No. 8 | colorless | same as left | same as left | same as left | same as left |

It is apparent from the Table that the present compounds have a remarkable effect.

EXAMPLE 12

To 50 parts of a flame-resisting unsaturated polyester resin were added 0.25 part of UVA No. 1 and 0.5 part of hardening agent (BPO), and the mixture was hardened in a mold at 70° C. for 1 hour and then at 120° C for 2 hours. Thus, test pieces were prepared.

The test pieces were exposed in a weather-O-meter under the condition below described and then measured for the degree of staining by means of a spectrophotometer (made by Shimazu Seisakusho Co., Ltd.). The results are shown in Table 6.

Exposure condition in weather-O-meter:

| -continued | |
|---|---|
| Weather-O-meter WE-6XC-HC (made by Toyo Rika Kogyo Co., Ltd.). | |
| shower time | 18 min/120 min. |
| temperature (inner) | 42° C |
| humidity - on shower | 98 % RH |
| humidity - no shower | 35 % RH |

Table 6

| | Exposure time | | | |
|---|---|---|---|---|
| Wavelength | 500 hrs. | | 1,000 hrs. | |
| UVA | T450 | T650 | T 450 | T650 |
| No addition | 23 | 8 | | 6 |
| UVA No. 1 | 5 | 0 | 2 | 0 |

$$\text{degree of staining} = \left[1 - \left(\frac{\text{transmittance after exposure}}{\text{transmittance before exposure}}\right)\right] \times 100$$

$$= T\lambda$$

The results mean that the present compound has an excellent protective effect against ultraviolet rays.

EXAMPLE 13

A mixture of 100 parts of ethylene-vinyl acetate copolymer (EVA) and 0.5 part of UVA No. 3 was kneaded on a 6-inch roller at 120° C for 5 minutes. The resulting sheet was cut into chips and the chips were molded into sheet of 1 mm in thickness under a pressing condition of 50 kg/cm² at 180° C. The sheet was then cut into dumb-bell No. 1 test pieces and exposed outdoors.

After the exposure, the test pieces were measured for the tensile strength retention and elongation retention on an extensometer. The results are shown in FIG. 4 (tensile strength retention) and FIG. 5 (elongation retention). The tension test condition is as follows.

| extensometer Strography-C | (made by Toyo Seiki Co., Ltd.) |
|---|---|
| tension rate | 500 mm/min |
| tension temperature | 20° C |

In the FIGS. (1), (2) and (3) are a curve obtained with the present compound UVA No. 3, the well known compound 1, and a blank test, respectively. The ordinate represents the retention (%) and the abscissa the exposure time (year).

EXAMPLE 14

A mixture of 100 parts of a high density polyethylene (medium pressure process) and 0.2 part of UVA No. 1 or UVA No. 14 was kneaded on a 6-inch roller at 140° C for 10 minutes and then formed into sheet. The sheet was pelletized and the pellets thus obtained were formed into sheet of 0.5 mm in thickness by pressing at 160° C, 100 kg/cm² for 5 minutes. The sheet was cut into dumb-bell No. 1 test pieces which were then exposed in a weather-O-meter. After the exposure, the test pieces were measured for the tensile strength retention and elongation retention on an extensometer. The results are shown in FIG. 6 (tensile strength retention) and FIG. 7 (elongation retention). The exposure condition on the weather-O-meter and tension test condition are as follows.

| | |
|---|---|
| Exposure test condition: | |
| Weather-O-meter WE-6XC-HC (made by Toyo Rika Kogyo Co., Ltd.) | |
| shower time | 18 min/120 min |
| temperature (inner) | 42° C |
| humidity - on shower | 98 % RH |
| humidity - no shower | 35 % RH |
| tension test condition: | |
| extensometer Strography-C | (made by Toyo Seiki Co., Ltd.) |
| tension rate | 50 mm/min |
| tension temperature | 20° C |

In the FIGS. (1), (2) and (3) are a curve obtained with the present compound UVA No. 1, UVA No. 14 and a blank test, respectively. The ordinate represents the retention (%) and the abscissa the exposure time (hour).

The present compounds other than No. 1 and No. 14 showed the same good results.

EXAMPLE 15

A mixture of 100 parts of a low density polyethylene and 0.2 part of UVA was kneaded on a 6-inch roller at 160° C for 10 minutes and then formed into sheet. The sheet was pelletized and the pellets thus obtained were formed into sheet of 0.5 mm in thickness by pressing at 160° C, 150 kg/cm² for 5 minutes. The sheet was cut into dumb-bell No. 1 test pieces which were then exposed in a weather-O-meter. After the exposure, the test pieces were measured for the elongation retention on an extensometer. The results are shown in FIG. 8. The exposure condition on the weather-O-meter was the same as described in Example 14.

| | |
|---|---|
| Tension test condition: | |
| extensometer Strography-C | (made by Toyo Seiki Co., Ltd.) |
| tension rate | 100 mm/min |
| tension temperature | 20° C |

In the FIGS. (1), (2) and (3) are a curve obtained with the well known compound 1, the present compound UVA No. 4 and a blank test, respectively. The ordinate represents the retention (%) and the abscissa the exposure time (hour).

The present compound gives an excellent effect to the physical properties of the sheet.

EXAMPLE 16

A mixture of 100 parts of polypropylene (density 0.96) and 0.2 part of ultraviolet absorbers was kneaded on a 6-inch roller at 185° C for 10 minutes and then formed into sheet. The sheet was cut into chips and the chips obtained were molded into sheet of 1 mm in thickness by pressing at 210° C and 50 kg/cm². The sheet thus obtained was exposed for 500 hours in a weather-O-meter and then the appearance of the sheet was observed. Separately from this, the test pieces were tested by the bending test at a certain time interval during the exposure, and the period of time which had elapsed until the test pieces were broken by the test was measured. The results are shown in Table 7.

Table 7

| UVA No. | Initial staining | Appearance after 500 hrs' exposure | Bending test (exposure time (hr)) |
|---|---|---|---|
| No addition | standard | small cracks all over the surface | 400 |
| No. 1 | same as no addition | no change | 800 |
| No. 4 | " | " | 850 |
| No. 7 | " | " | 700 |

The Table shows that the present compounds have an excellent protective effect against ultraviolet rays.

EXAMPLE 17

A mixture of 100 parts of polystyrene and 0.4 part of UVA was pelletized through a 30 mm φ extruder. The pellets thus obtained were molded into test pieces by means of the 1S-50 3-ounce injection molding machine (made by Toshiba Co., Ltd.). The test pieces were exposed in the Acme Fade-O-meter (made by Shimazu Seisakusho Co., Ltd.) and then were tested, on a spectrophotometer, for the transmittance at the wavelengths, 420 mμ, 560 mμ and 680 mμ, of the visible light. The yellowing index was calculated from the transmittance according to the following equation.

$$\text{Yellowing index} = \frac{(T_{420} - T'_{420}) - (T_{680} - T'_{680})}{T_{560}} \times 100$$

T': transmittance of exposed test pieces at 420 mμ and 680 mμ

T: transmittance of unexposed test pieces

Figure 9:
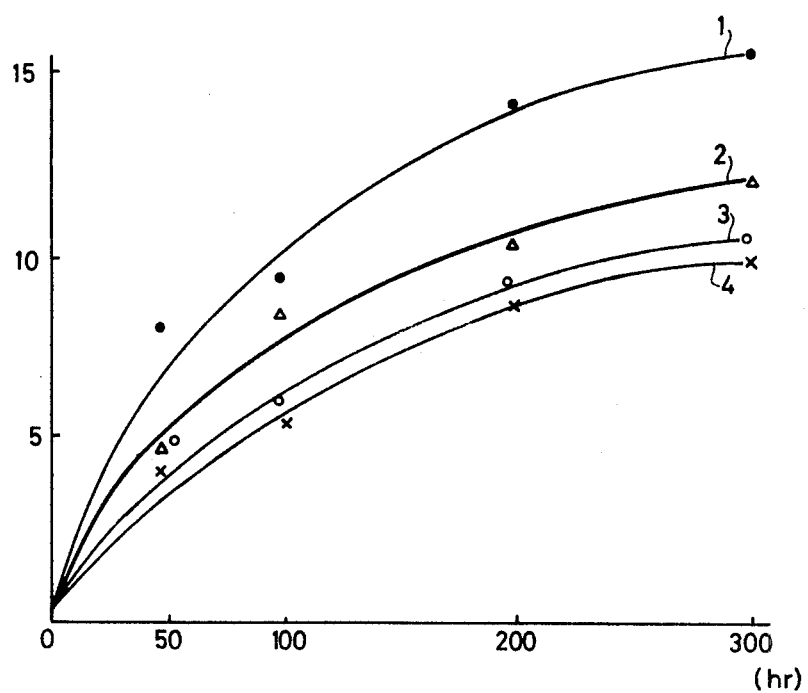

The results are shown in FIG. 9, which show that the present compounds have an excellent effect.

In the FIGS. (1), (2), (3) and (4) are a curve obtained with no addition, the well known compound 1, the present compound UVA No. 1 and UVA No. 10, respectively. The ordinate represents the yellowing index and the abscissa the exposure time (hour) on the Acme Fade-O-meter.

EXAMPLE 18

A solution comprising 82.7 parts of acetone, 2.0 parts of dibutylphthalate, 0.3 part of UVA No. 10 and 15 parts of acetyl cellulose which has 2.5 acetoxy groups on the average per glucose unit, was applied onto glass plate to form into film of 0.04 mm in thickness.

The film thus obtained was exposed in a fade-O-meter for 1,000 hours, and then tested for the brittleness. The results are as follows.

| Ultraviolet absorbers | Ease of bending |
|---|---|
| UVA No. 10 | easy |
| No addition | brittle (broken down) |

The film containing the ultraviolet absorber showed only a little loss in the transmittance in the course of exposure.

EXAMPLE 19

A mixture of 100 parts of methyl methacrylate, 0.5 part of UVA No. 17 and 0.2 part of lauroyl peroxide was polymerized at 50° C to 70° C to form into sheet of 2 mm in thickness.

The sheet thus obtained could be used as a colorless filter for ultraviolet rays.

EXAMPLE 20

A mixture of 100 parts of granular polycaprolactam and 1 part of UVA No. 19 was molten at 255° C in an autoclave under removal of air. The melt was extruded through a die under the pressure of nitrogen gas.

The resulting solid mass absorbs ultraviolet rays and therefore can be used for preparation of substances which do not transmit ultraviolet rays.

Replacement of the polycaprolactam by polyhexamethylene adipamide gives also substances which do not transmit ultraviolet rays.

EXAMPLE 21

Fine powder of the ultraviolet absorber No. 9 was mixed with a disperse dye for polyester fibers in an amount of 5% by weight based on the dye, and then the mixture was dyed on Teloron cloth according to the usual methods. The dyed cloth obtained had a light fastness improved by 1 to 2 ratings, compared with the cloth dyed without using the ultraviolet absorber. The same result was also obtained by adding the aqueous dispersion of the present compound which had been prepared with a surfactant according to the usual methods to the dyeing bath. The same or similar application method to the above mentioned ones can be applied to dyeing of other synthetic fibers thus improving the light fastness of dyed materials.

EXAMPLE 22

Polyacrylonitrile fibers were treated in a bath (liquor ratio 1:30) containing the ultraviolet absorber No. 4 of 0.03% by weight based on the fibers at 95° C to 100° C for 60 minutes. Then, the fibers were soaped, rinsed and dried. The materials thus treated had an extremely improved light fastness compared with those treated without using the ultraviolet absorber. Additionally, the treatment above mentioned may be carried out in combination with dyes, fluorescent brightening agents or oxidizing agents such as sodium chlorite, and thus the light fastness of the dyes or agents may also be improved by 1 to 2 ratings.

REFERENCE EXAMPLE 1

(Staining test by heating)

About 1.0 g of ultraviolet absorbers was placed in a test tube and heated in an oil bath at 270° ± 5° C for 30 minutes. After allowing it to cool, 500 mg of the absorber was dissolved in 50 ml of dioxane (solution A). Separately from this, 500 mg of the untreated absorber were dissolved in 50 ml of dioxane (solution B). The two solutions were tested for the transmittance at the wavelengths, 450 mµ, 500 mµ and 550 mµ, of the visible light.

The reduction percentage of transmittance was calculated for each wavelength according to the following equation.

$$\frac{T(\text{before heating}) - T(\text{after heating})}{T(\text{before heating})} \times 100$$

T: transmittance

The degree of staining which represents deterioration of absorbers by heating was evaluated based on the reduction percentage of transmittance. The results are shown in Table 8.

The results show that the present compounds have an extremely high resistance to heat.

The resistance to heat of each derivative is represented by the reduction percentage of transmittance at the three wavelengths, and lower values of the percentage mean a higher resistance to heat.

Table 8

| UVA No. | T450 | T500 | T550 | Evaluation |
|---|---|---|---|---|
| 1 | 11.4 % | 6.7 % | 3.1 % | +++ |
| 2 | 13.5 | 8.2 | 3.5 | +++ |
| 3 | 9.7 | 4.9 | 2.9 | +++ |
| 4 | 10.8 | 6.6 | 3.0 | +++ |
| 5 | 23.1 | 9.5 | 6.3 | ++ |
| 7 | 30.3 | 18.2 | 10.5 | ++ |
| 15 | 16.5 | 9.1 | 6.2 | +++ |
| 16 | 31.2 | 16.5 | 7.3 | ++ |
| 18 | 35.8 | 20.1 | 11.3 | ++ |
| Well known compound 1 | 60.3 | 29.8 | 16.7 | o − + |
| Well known compound 2 | 70.9 | 47.5 | 30.2 | o |

Note:
Larger number of the symbol + means a higher resistance to heat.

REFERENCE EXAMPLE 2

(Non-volatility test)

The present compounds and well known compounds were measured for the volatility on a thermobalance. The results are shown in FIG. 1. The ordinate represents the reduction percentage (%) and the abscissa the heating temperature (°C).

| | |
|---|---|
| Apparatus: | |
| Standard differential thermobalance (Rigaku Denki Co., Ltd.) | |
| Test condition: | |
| TGA sensitivity | 10 mg |
| Heating rate | 10° C/min |
| Chart speed | 8 mm/min |
| Sensitivity of recorder | |
| Temperature curve | 20 mV |
| Reduction curve | 10 mV |

Test sample:
(1) Well known compound 2 in Example 1
(2) Well known compound 1 in Example 1
(3) Present compound UVA No. 3
(4) Present compound UVA No. 1

The experimental results show that the present compounds have an excellent non-volatility, which means that this property is very advantageous for application to resins which are to be processed at high temperatures.

What is claimed is:
1. A compound of the formula

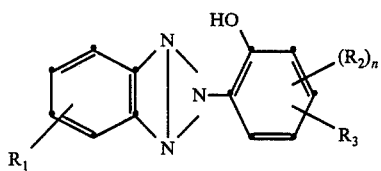

wherein R₁ is hydrogen or a halogen atom, R₂ is

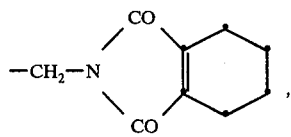

R₃ is hydrogen, a $C_1$–$C_{18}$ alkyl, a $C_5$–$C_7$ cyclo alkyl or phenyl $C_1$–$C_3$ alkyl, and *n* is an integer of 1 or 2.

2. The compound according to claim 1, wherein R₁ is hydrogen or chlorine.

3. The compound according to claim 1, wherein R₃ is an alkyl having 1 to 4 carbon atoms.

4. A compound of the formula,

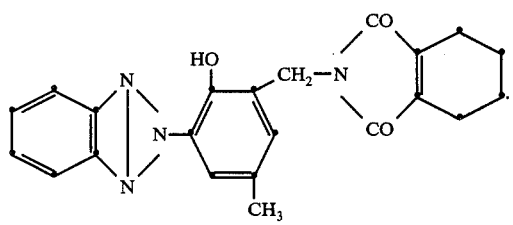

5. A compound of the formula,

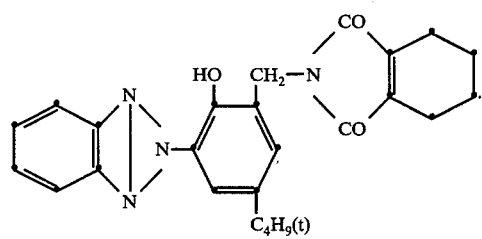

6. A compound of the formula,

7. A compound of the formula,

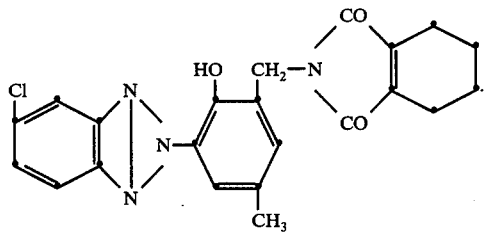

8. A compound of the formula,

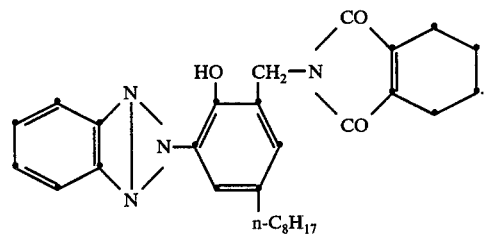

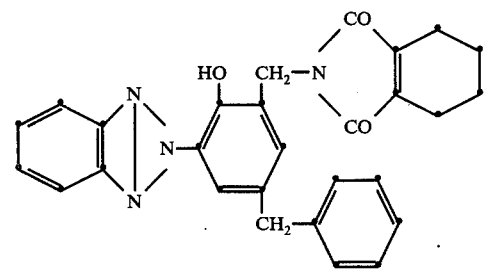

9. A compound of the formula,

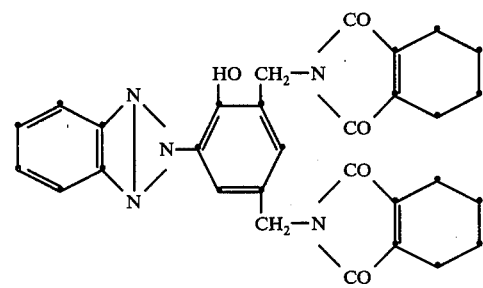

10. A compound of the formula:

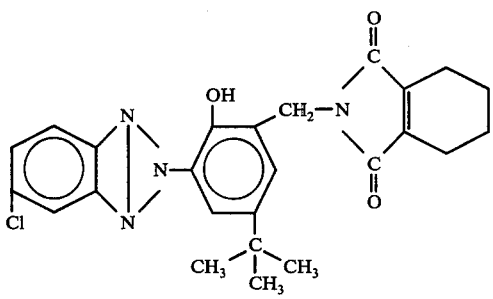

* * * * *